US009945764B2

(12) United States Patent
Yeomans

(10) Patent No.: US 9,945,764 B2
(45) Date of Patent: Apr. 17, 2018

(54) METHOD OF AND APPARATUS FOR DETERMINING THE CARBON CONTENT OF SOILS

(71) Applicant: Allan James Yeomans, Gold Coast (AU)

(72) Inventor: Allan James Yeomans, Gold Coast (AU)

(*) Notice: Subject to any disclaimer, the term of this patent is extended or adjusted under 35 U.S.C. 154(b) by 318 days.

(21) Appl. No.: 14/432,429

(22) PCT Filed: Oct. 8, 2013

(86) PCT No.: PCT/AU2013/001151
§ 371 (c)(1),
(2) Date: Mar. 30, 2015

(87) PCT Pub. No.: WO2014/053028
PCT Pub. Date: Apr. 10, 2014

(65) Prior Publication Data
US 2015/0247787 A1    Sep. 3, 2015

(30) Foreign Application Priority Data

Oct. 5, 2012 (AU) .............................. 2012904343
Mar. 28, 2013 (AU) .............................. 2013901073

(51) Int. Cl.
*G01N 31/12* (2006.01)
*G01N 5/04* (2006.01)
*G01N 33/24* (2006.01)

(52) U.S. Cl.
CPC .............. *G01N 5/04* (2013.01); *G01N 5/045* (2013.01); *G01N 31/12* (2013.01); *G01N 33/24* (2013.01)

(58) Field of Classification Search
CPC ........................................................ G01N 31/12
See application file for complete search history.

(56) References Cited

U.S. PATENT DOCUMENTS 2,371,637 A * 3/1945 McDermott ........... G01V 9/007
  436/160
4,699,002 A * 10/1987 Rockley ................ E21B 49/005
  73/152.07

FOREIGN PATENT DOCUMENTS

JP    2003-240625 A    8/2003

OTHER PUBLICATIONS

Written Opinion dated Dec. 6, 2013.

* cited by examiner

*Primary Examiner* — Robert R Raevis
(74) *Attorney, Agent, or Firm* — Wood, Phillips, Katz, Clark & Mortimer

(57) ABSTRACT

A method of and apparatus (41) for determining the organic carbon content of soil in heated air or gas is forced through a soil sample (36) to burn off or oxidize organic carbon in the sample with the change of weight of the sample (36) indicating the carbon content in the soil sample (36) and thus the soil from which the sample (36) is taken. The apparatus (41) includes a housing (47) in which one or more soil samples (36) may be located, a heater unit (51) for heating the air or gas for passage through the soil samples (36) to burn off organic materials therein including organic carbon. The apparatus (41) also includes a weighing device (76) which enables the change of weight of the soil samples (36) to be determined while the samples (36) remain within the housing (47).

17 Claims, 8 Drawing Sheets

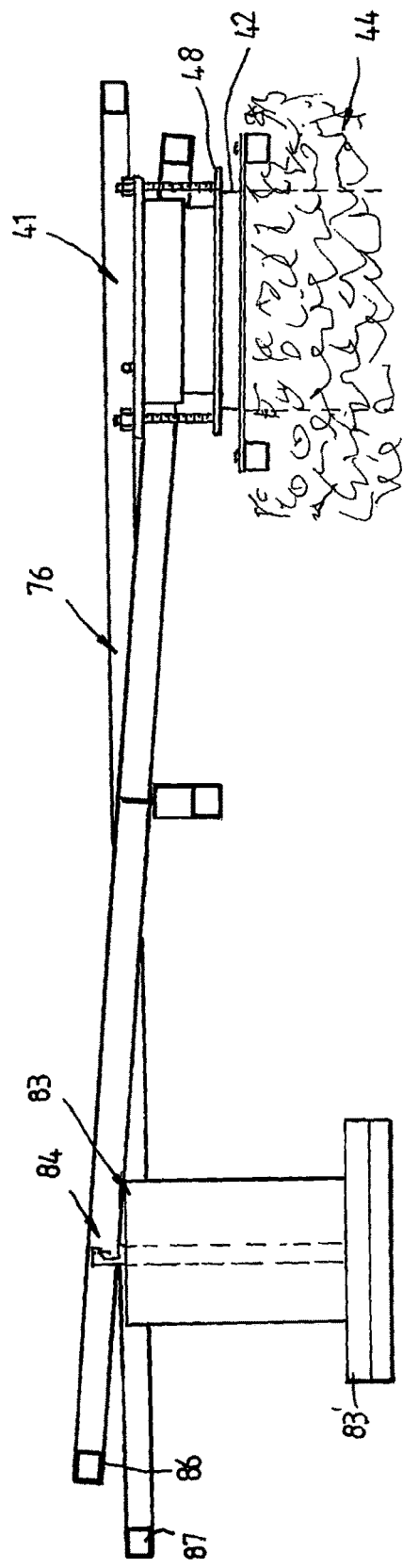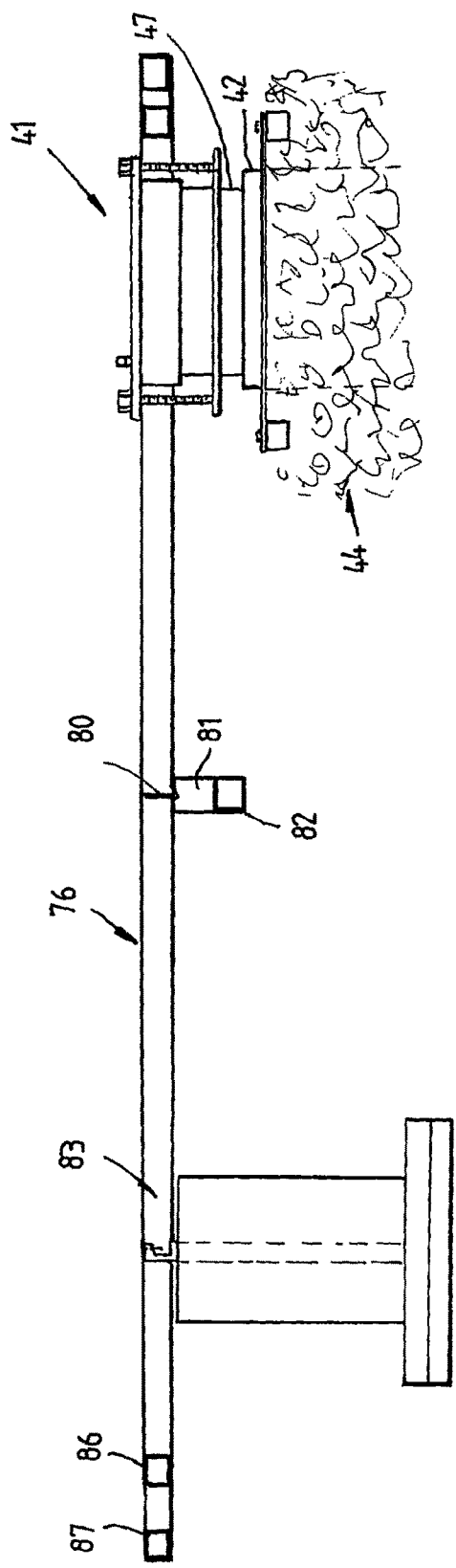
FIG. 12
FIG. 13

METHOD OF AND APPARATUS FOR DETERMINING THE CARBON CONTENT OF SOILS

TECHNICAL FIELD

This invention relates to a method of and apparatus for determining the carbon content of soils and in a particular aspect to a method of drying and heating a sample of soil to enable the carbon content in the soil sample and variations in the carbon content in the soil sample over time to be determined. The present invention also relates to a method of and apparatus for the in situ determination of the carbon content of soil by measuring the change of weight of a soil sample as a result of the heating process.

BACKGROUND ART

Carbon dioxide in the atmosphere generally considered to be caused by the use of fossil carbon fuels forms an insulating gas layer or blanket which determines the average temperature of the Earth's biosphere. Due to the build up of the carbon dioxide layer in the atmosphere, the biosphere is overheating as a result of the "greenhouse" effect of this layer thereby producing global warming. Reducing the rate at which the layer is increasing in thickness for example by substantially reducing the rate of use of fossil carbon fuels would be insufficient in itself to reduce this heating effect or stop progressive global warming.

The only current practical, economic and efficient way of removing accumulated excess greenhouse gasses is to sequester carbon dioxide in agricultural soils. In this process carbon in atmospheric carbon dioxide is converted into carbon in organic matter in the soil known as soil humus. Production of soil humus which makes poor soils fertile reduces the need to use strong agricultural chemicals which tends to hinder rapid formation of fertile soil.

To encourage the use of carbon dioxide sequestration, a scheme has been proposed whereby farmers are paid remuneration based on the tonnage of the carbon dioxide removed from the air by converting it into soil humus or organic matter. One disadvantage of this scheme is that it is difficult to measure organic carbon content in soil.

Current methods for measuring carbon content in the soil typically involve the taking of a small sample of soil and testing that sample using chemical analysis or heating in an oven to provide an indication of carbon content in a particular area. The results from these tests are then extrapolated to produce a measure of carbon content over a whole area from which the sample is taken. The current methods are not particularly effective or accurate.

It would be desirable therefore if an improved method and apparatus was available which facilitated the calculation of organic carbon content in soil and variations in organic carbon content in soil over time.

SUMMARY OF THE INVENTION

The present invention thus provides in one preferred aspect, a method of determining the carbon content of soil and/or variations or changes in carbon content, said method including the steps of taking a sample of said soil, forcing heated gas through said soil sample to remove carbon from said soil sample, and determining from the change of weight of the soil sample the carbon content in the soil sample. The present invention also provides a method of removing moisture from the soil sample by forcing heated gas through the soil sample prior to the carbon removal process. The temperature of the heated gas for removal of moisture typically is at or slightly above the boiling temperature of water such as a temperature of about 100° C. to 115° C. The temperature of gas for removing carbon from soil is a temperature of up to about 550° C. which is sufficient for the combustion and oxidisation of organic materials including organic carbon in the soil. Typically the gas comprises air but may comprise oxygen or other gas or gases which include some oxygen to ensure burning off of organic materials in the soil samples. The terms "carbon" and "carbon content" as used throughout the description and claims in relation to the soil and soil samples which are subject of the method and apparatus of the present invention mean organic carbon and organic carbon content respectively.

The method referred to above uses a loss on ignition (LOI) principle in which a sample of material is strongly heated which causes volatile substances in the sample to escape until the mass of the sample ceases to change. In the present invention, heating of the soil sample is achieved by passing heated air or gas through the soil sample for a sufficient time and at selected test temperatures until the weight of the soil sample ceases to change, the loss of weight being due to organic material including carbon being burnt off and oxidised and being indicative of carbon content in the soil. Preferably, the gas flow through the soil sample is controlled to control the temperature of the soil sample to ensure that the temperature thereof does not exceed a predetermined temperature or range of temperatures. Controlling the gas flow through the sample of soil controls oxygen flow through the sample and therefore controls the burning of materials in the sample and ensures that the temperature of the sample does not exceed the predetermined temperature or range of temperatures.

Preferably the method involves the step of supporting the sample of soil on one or more gas permeable means such that gas can be forced through the soil sample. The gas permeable means may comprise a grid or grating. The gas permeable means may additionally comprise a gas permeable fabric or other material.

The method of the invention may also include the step of providing additional means for heating or for assisting the distribution of heat through the soil sample. Such means may comprise a heat jacket or a heating device which surrounds the soil sample to ensure even distribution of heat through the soil sample.

The method of the invention may also include the step of monitoring the temperature of gas which has passed through the soil sample so as to enable determination of the moisture content and carbon content in the soil sample. Should the temperature of the soil sample as monitored increase towards or beyond the predetermined temperature or range of temperatures, the flow of gas is restricted to restrict oxygen intake and prevent excessive burning of organic carbon type materials in the soil sample.

The present invention in a further aspect provides apparatus for determining the carbon content of soil and/or variations of the carbon content in soil, said apparatus comprising an housing defining a chamber, means for supporting one or more samples of said soil within said chamber, means for forcing heated gas through said chamber and the soil sample or samples therein to remove organic carbon from the soil and means for measuring the change of weight of said soil sample or samples to provide an indication of carbon content in the soil. The apparatus of the invention uses a loss on ignition (LOI) technique or principle to determine carbon content in a soil sample. The apparatus of the present invention may also be used to remove moisture from the soil sample or samples prior to the removal of carbon by forcing heated gas at lower temperatures through the sample or samples.

Preferably, a plurality of soil samples are used and the soil samples are arranged within the chamber in series such that heated gas can be passed through the respective soil samples in turn. Preferably the housing and thus chamber are of elongated form and have a central longitudinal axis with an inlet at one end for heated gas and an outlet at the other end. Preferably respective soil samples are arranged longitudinally along the axis of the chamber. Preferably the housing is of a tubular configuration and thus the chamber is of a circular cross section.

Preferably respective gas permeable means are provided to support the one or more soil samples within the chamber. Suitably the gas permeable means form barriers which extend diametrically of the chamber. The gas permeable means may comprise a soil sample holder which includes a grid or grating. The grid or grating suitably is in a similar configuration to, and size of the cross section of the chamber. The grid or grating therefore is preferably of a circular configuration. Preferably where a plurality of soil sample holders are used, they are interengaged with each other. For this purpose, each soil sample holder includes a pin or shaft which extends centrally from the grid or grating to extend longitudinally of the chamber in use and the pins or shafts of adjacent soil sample holders are engaged with each other. Suitably, the pins or shafts have a hollow longitudinal portion extending from the grid or grating, the hollow portion being adapted to receive the leading end of a pin or shaft of an adjacent holder so that the soil sample holders can be arranged in a "piggy-back" relationship.

Alternatively, all the soil sample holders may be supported on a common pin or shaft which extends centrally and longitudinally of the chamber in use. The soil sample holders may be adjustable to any position along the common pin or shaft or may be set at respective predetermined locations along the pin or shaft. For example, the pin or shaft may be provided with a series of spaced apart rebates or holes in or through its outer surface and stop means are provided on a holder for cooperation with a rebate or hole to locate a soil sample holder along the shaft. The stop means may comprise a stop pin carried by a soil sample holder which can engage with a selected rebate or hole. Each soil sample holder in this embodiment may include central sleeve or boss fixed to a grid or grating and which is capable of slidable engagement with the pin or shaft. The sleeve or boss may have an aperture through which a stop pin can be inserted for location in a rebate or hole in the common pin or shaft.

To maintain a soil sample on a grid or grating and prevent fine particles of soil escaping through the grid or grating, a gas-permeable material or pad may be supported on the grid or grating. The gas-permeable material or pad may comprise a fibrous material such as a glass fibre mat or other air permeable pliable fabric. Preferably the gas-permeable material forms or adopts a substantial cup-shaped configuration within the chamber. Preferably the gas-permeable material forms a substantial seal with the side wall of the chamber when the soil sample is held in or on the material, the soil urging the material into sealing contact with the side wall of the chamber to prevent or minimise gas escaping past the soil sample(s) without passing through the soil sample (s).

The means for forcing heated gas through the chamber, may comprise a heated gas source which generates a flow of heated gas which is directed longitudinally of the chamber from one end to the other end of the chamber. Alternatively, a gas heating device may be provided at one end of the chamber and means may be provided at the opposite end of the chamber for drawing gas through the air heating device. The gas heating device may comprise a heating element. The heating element may be provided within a shroud or heat tube adjacent the one end of the chamber. The means for drawings gas through the air heating device may comprise a suction pump or the like which can draw gas through the shroud or tube to heat the gas and then draw the heated gas through the chamber containing the soil sample(s).

A gas jacket may be provided around the housing and heated gas can be directed into the jacket to ensure even heating of the soil sample(s) within the chamber and insulate the chamber from the external atmosphere. Preferably the gas jacket is surrounded by an insulating material such as rock wool to prevent loss of heat from the apparatus and gas jacket.

Suitable temperature sensing means may be provided downstream of one or more of the sample holders to monitor the temperature of air after it passes through the soil sample (s). Where the soil sample holders are mounted on a single hollow pin or shaft, openings or slots may be provided in the pin or shaft through which one or more temperature sensors may be received or through which one or more temperature sensors may project. Wiring for the or each sensor may extend longitudinally within the hollow pin or shaft.

Means are suitably provided for weighing the housing containing the soil sample(s) before and after the carbon removal process to enable calculation of the change of weight in the soil sample(s), whilst they remain in situ within the housing to provide an indication of carbon content in the soil sample(s), The housing may be suspended from the weighing means and remain connected to the housing means before during and after the heating process.

In another embodiment, means may be provided for determining the change of total weight of the housing and soil sample(s), therein consequent upon heating of the soil sample(s) to provide an indication of change of weight of the soil sample(s) in situ within the housing and therefore the carbon content of the soil. The means for determining the change in weight may comprise a beam balance having a beam or lever which has a central fulcrum, means on one side of the fulcrum for supporting the housing and means on the opposite side of the fulcrum for carrying a variable counter or balance weight. The housing may be suspended from the beam on one side of the fulcrum such as by means of a knife edge suspension. Preferably, the housing includes one or more hanger members to enable the housing to be suspended via the knife-edge suspension from the beam. Preferably, the hanger assemblies comprise a pair of diametrically spaced hangers provided on the annular ring of the housing. Preferably the housing remains connected to the beam during the heating and oxidation process such that at the end of that process, the balance beam can be used for determining the total change in weight of the housing including the soil samples without removing the soil samples from the housing.

The housing may be located substantially coaxially with clearance within an upright outer tubular member and the housing being is capable of being moved longitudinally of the outer tubular member in a first direction during balancing of said beam. The housing may include means adapted for cooperation with the outer tubular member to limit movement of the housing in a direction opposite the first direction. Such means may comprise an annular ring adapted to seat on the upper end of the outer tubular member to close the upper end of the annular space between the housing and outer tubular member.

A heating unit for generating a flow of heated gas may be located within the housing adjacent an upper end thereof. The heater unit may have an inlet for connection to a source of pressurised gas. Preferably the heater unit includes a heating element and one or more passages are provided to direct gas from the source of pressurised gas past the heating element so that the gas can be heated for supply to the chamber for passage through the soil samples. Preferably the heater unit includes a series of coaxial tubes which define the one or more passages. Preferably a former assembly is provided around which the heating element may be wound. The former assembly may include a plurality of circumferentially spaced former elements which extend longitudinally of the tubular member and the heating element which is typically wire is wound circumferentially around the former elements.

The heater unit may include an upper collar and the collar is suitably adapted to be releasably sealed to the housing in which the soil samples are located. Preferably the collar carries an internal O-ring adapted to seal against the outer surface of the housing. The heating unit may also include further sealing means at its lower end for sealing engagement with the inner surface of the housing. Preferably the coaxial tubes are arranged such that gas from the pressurised gas source flows in a serpentine manner through the heating unit. One of the coaxial tubes of the hearing unit may comprise a central outlet tube through which the heated gas exits the heating unit.

Preferably in this embodiment, an air jacket is not employed to provide additional heating to the samples. Instead, an electrical heating element may be provided around the outer tubular member in the region of the soil samples. The outer tubular member is suitably supported in its upright position and can be surrounded by insulating material. When the annular ring seats on the upper end of the outer tubular member, it closes the space between the housing and outer tubular member to prevent upward gas flow from the region between the housing and outer tubular member. The clearance between the housing and outer tubular member allows free longitudinal movement of the housing within the tubular member in the first direction during subsequent weighing. Thus at the end of the heating process, organic materials including organic carbon in the soil samples will have been burnt off or oxidised and consequently, the soil samples will lose weight. To achieve balance of the balance beam, weight will be required to be removed from the counter or balance weight and that removed weight will be indicative of organic carbon content in the soil samples.

The present invention in a further aspect provides a method of determining change in weight of a soil sample or samples to indicate the carbon content thereof, said method comprising the steps of locating said soil sample or samples within a housing, subjecting said soil sample or samples in said housing to heating to remove carbon from said soil sample or samples and measuring the change in total weight of said housing and said soil sample or samples due to said heating of said soil sample or samples without removing said sample or samples from said housing. Suitably the soil sample or samples are heated by passing a heated gas through the soil sample or sample for a sufficient time and at selected temperatures or range of temperatures until the weight of the soil sample ceases to change.

Preferably the method includes the step of initially drying the sample or samples and measuring the change in weight of the sample or samples after drying and after the carbon removal process to provide an indication of carbon content of the initial soil sample or samples.

DETAILED DESCRIPTION OF THE PREFERRED EMBODIMENT

Reference will now be made to the accompanying drawings which illustrate preferred embodiments of the invention and wherein FIG. 1 is a schematic cross-sectional view of apparatus for heating soil samples according to an embodiment of the invention;

FIGS. 12 and 13 are schematic views along line B-B of FIG. 11 showing the soil sample weighing apparatus in two modes of operation;

DETAILED DESCRIPTION OF THE PREFERRED EMBODIMENT

Figure 1:
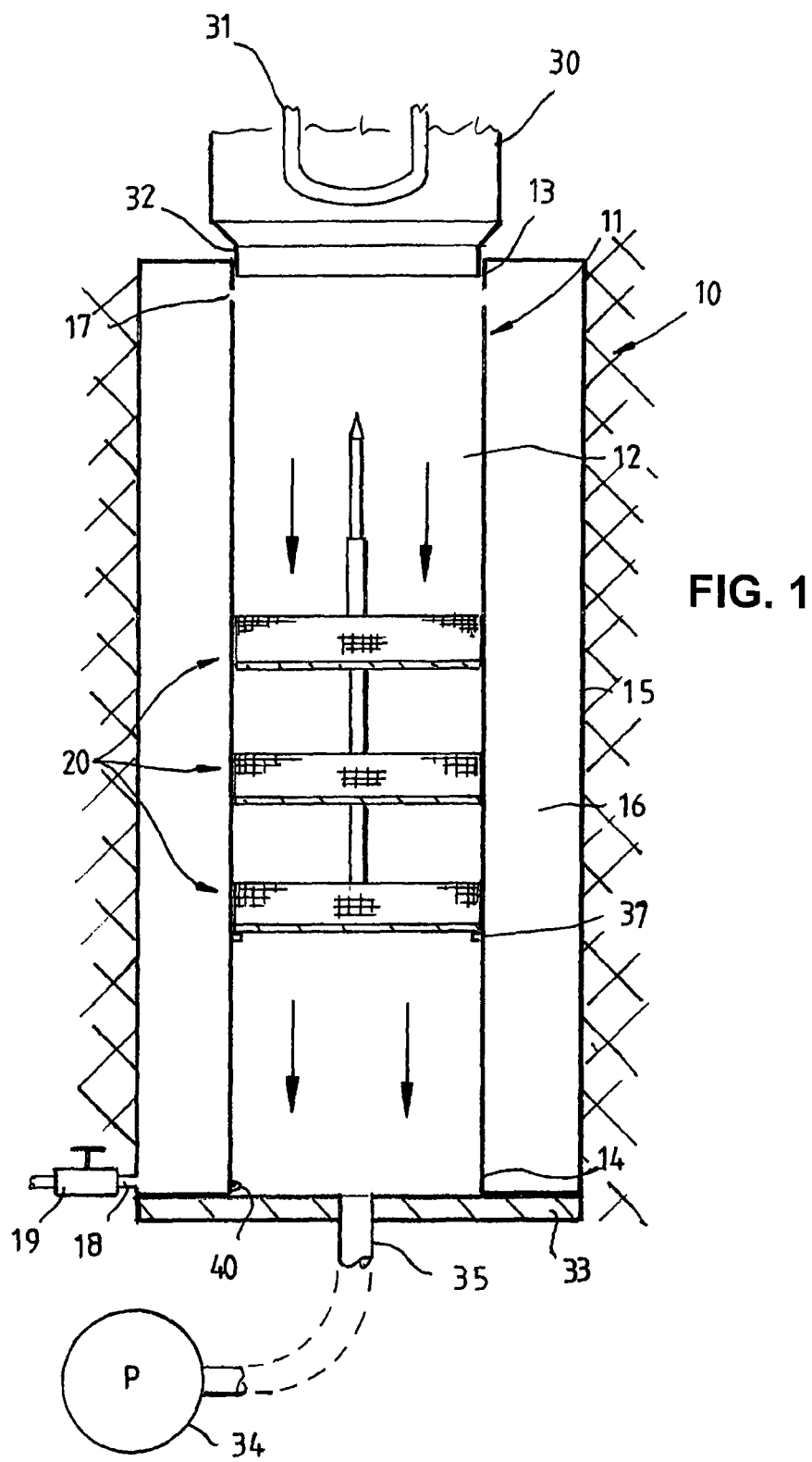

Referring to the drawings and firstly to FIG. 1, there is illustrated apparatus 10 which may be used for heating a sample or samples of soil for the purpose of determining the carbon content thereof. The apparatus 10 comprises an elongated housing 11 which is of a circular cross section so as to be of a tubular configuration and which defines an elongated heating chamber 12 open at opposite ends 13 and 14 of the housing 11. Surrounding and arranged coaxially relative to the housing 11 is an, outer tubular member 15 which defines with the housing 11 an hollow annular chamber 16 which can form a heat jacket which surrounds the housing 11. One or more inlet openings 17 are provided into the heat jacket chamber 16 adjacent the upper end 13 of the drying chamber 12 whilst an outlet 18 is provided at the lower end 14 of the chamber 12, the outlet 18 being controlled by a valve 19. Suitable known insulating material such as rock wool may be provided around the outer side of the tubular member 15 as indicated in cross hatching. The insulting material may be contained within any external container.

Figure 2:
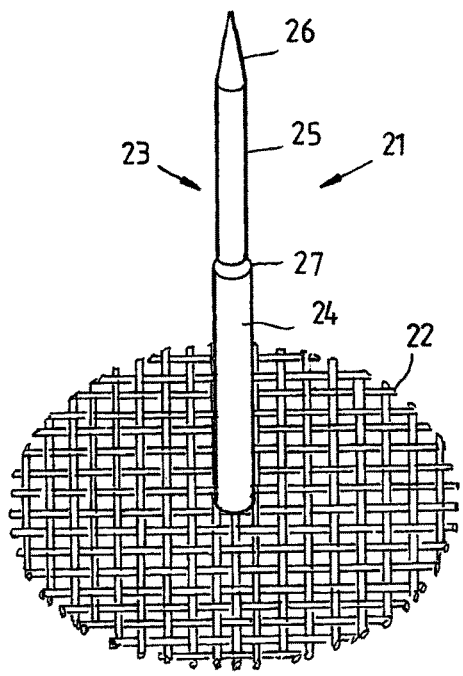
FIG. 2 illustrates a soil sample holder for use in the apparatus of FIG. 1.

A series of soil sample holder assemblies 20 are arranged in use within the chamber 12, each soil sample holder assembly 20 including as shown in FIG. 2, a rigid holder 21 comprising an air or gas permeable grid or mesh member 22 of circular configuration and of slightly smaller diameter than the diameter of the chamber 12 and a central support shaft 23 rigid with the member 22, the shaft 23 having a lower hollow section 24 and an upper section 25 which may be hollow or solid and which terminates in an upper point or tapered region 26. The upper section 25 is of a diameter smaller than the inner diameter of the hollow section 24 such that it may be slidably received within the lower hollow section 24 of a further support shaft 23 in a mating manner. The junction between the lower and upper sections 24 and 25 of the support shaft 23 defines a shoulder 27 upon which an adjacent upper holder 21 may seat as described further below. Alternatively and preferably the upper pin section 25 is of such a length that the point or tapered region 26 will abut the lower end of the upper section 25 of an adjacent holder 21.

Figure 3:
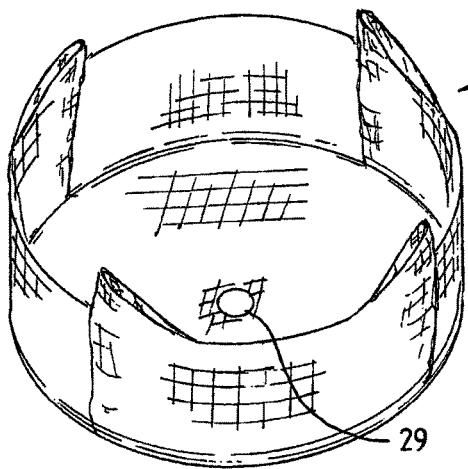
FIG. 3 illustrates an air or gas permeable cup for use with the soil sample holder.

To prevent escape of fine soil particles, the soil sample holder 21 may be used with a flexible cup shaped member 28 formed of a fabric of other pliable material which is air or gas permeable. The fabric or other pliable material preferably comprises an air or gas permeable material which can handle the temperatures encountered in the apparatus 10. A suitable material may comprise a woven fibreglass cloth. The member 28 may be formed or shaped from material which is initially in a flat form which can be folded into the generally cup-shaped configuration shown in FIG. 3. The cup shaped member 28 is also provided with a central opening 29 which can neatly but firmly receive the shaft 23 and substantially seal thereagainst.

For drying and heating of soil samples located within the chamber 12, hot gas typically air may be introduced into the upper inlet end 13 of the chamber 12 to be forced through the chamber 12. Alternatively and as illustrated, the apparatus 10 in this embodiment is used with a hollow heater tube or shroud 30 which is open at its opposite ends and in which an elongated heating element 31 is located (see also FIG. 5), the tube or shroud 30 having a lower end 32 adapted to be sealingly but releasably engaged with the inlet end 13 of the chamber 12. For this purpose, the end 32 may be slightly tapered to engage with the inner wall surface of the chamber 12. The tube or shroud 30 is mounted in a fixed position by any suitably mounting means.

To draw air through the chamber 12, a suction plate 33 is provided to engage with the end 14 of the chamber 12, the suction plate 33 being connectable to a suction source such as a suction pump 34 through a suction tube 35. It will be appreciated that in the configuration of FIG. 1 when a suction pressure is applied to the tube 35, air will be drawn through the heat tube or shroud 30 and chamber 12 in the direction of the arrows shown in FIG. 1. The suction plate 33 only remains in position whilst a suction pressure is applied although auxiliary connectors may also be provided to hold it in position. The suction plate 33 alternatively be secured permanently to the housing 11 or formed as part of the housing 11.

In use samples of soil 36 taken from an area where carbon content is to be determined is screened to remove all fibrous material such as plant and animal material not yet decomposed. The cup-shaped member 28 is formed by folding and is positioned over the support shaft 23 and slid therealong to seat on the grid 22 to form the holder assembly 20 and a soil sample 36 may then be deposited into the cup-shaped member 28.

The sample holder assembly 20 carrying the soil sample 36 is then inserted into the end 13 of the chamber 12 and slid longitudinally therealong to the required position defined by a stop 37 within the chamber 12. When the soil sample 36 is held on the holder assembly 20, the soil sample 36 will urge the pliable material of the member 28 radially outwardly so that it substantially seals against the inner surface of the chamber 12. This prevents hot air flowing through the chamber 12 from bypassing the soil sample 36. A further soil sample holder assembly 20 is then prepared as above and inserted into the chamber 12 via the end 13. This holder assembly 20 is slid along the chamber 12 so that the lower open shaft section 24 locates over the upper shaft section 25 of the lower sample holder assembly 20 until the point of the upper end 26 of the lower holder 21 abuts the lower end of the section 25 of the inserted holder assembly 20. Mating of the holder assemblies 21 relative to each other is facilitated by the tapered end 26 of the upper shaft section 25. A further sample holder 20 is also prepared and inserted into the chamber 12 to engage with the previously inserted holder 20 in the manner described above so that three soil samples 36 are held within the chamber 12 with the holder assemblies 20 interengaged in the manner shown in FIG. 4.

Figure 6:
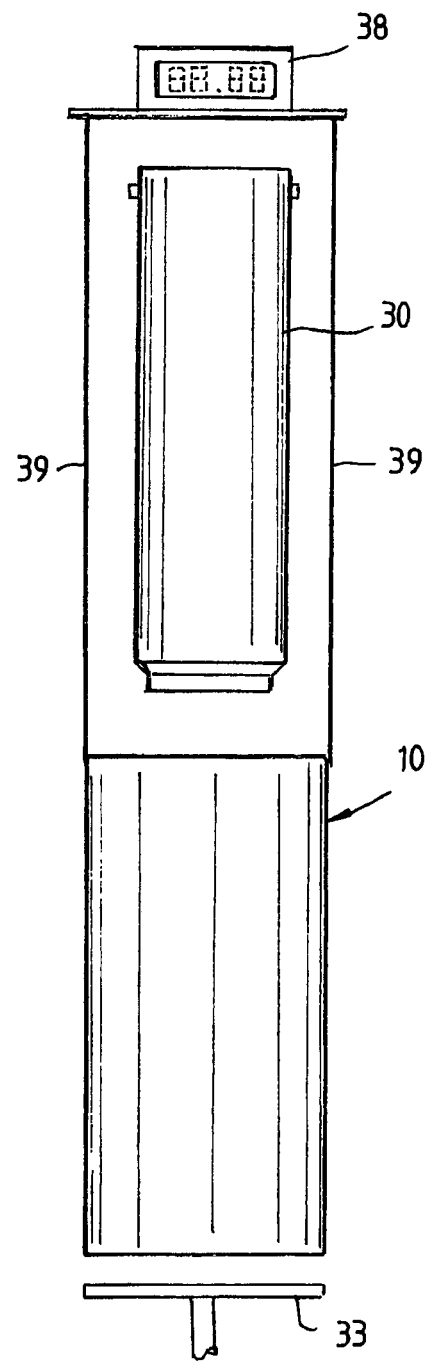
FIG. 6 is a side view illustrating the manner in which the soil samples and apparatus may be weighed in situ.

The housing 11 with installed sample holder assemblies 20 may then be weighed to provide an indication of the weight of the soil samples 36 prior to the drying process and/or before, during and after the carbon removal process. For determining the weight of the soil samples, the apparatus 10 may be suspended from a weighing device 38 as shown in FIG. 6 by elongated suspension elements 39 which allow weighing of the apparatus 10 and soil samples 36 in situ.

Figure 5:
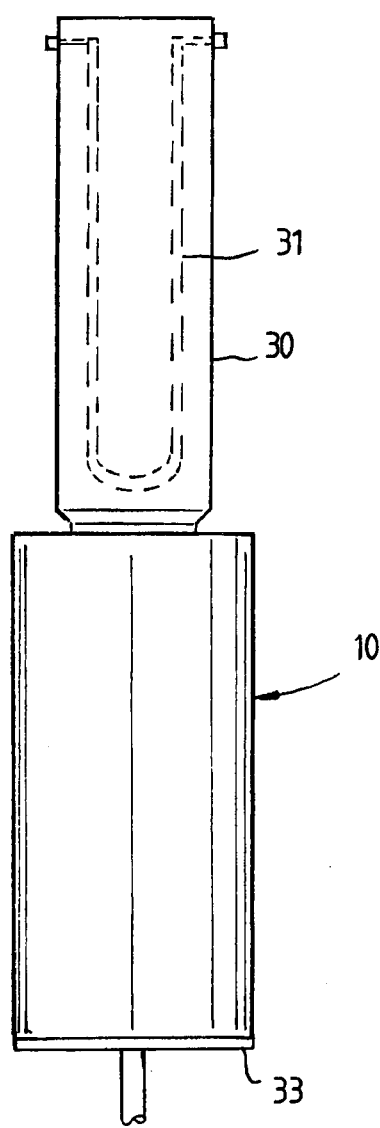
FIG. 5 is a side view showing the apparatus in a mode in which heating of the soil samples occurs.

For operation of the apparatus, the upper end 13 of the chamber 12 is engaged with the heat tube or shroud 30 and the suction plate 33 applied to the lower end 14 of the chamber 12 as shown in FIG. 5. Current is applied to the heating element 31 and when the suction pump 35 is operated, the suction plate 33 will be held against the end 14 of the chamber 12 and air will be drawn through the heat tube 30 and past the element 31 and then through the soil samples 35 at a temperature typically in the range of 110-530° C. In addition, a proportion of hot air is directed into the opening(s), 17 into the heat jacket 16 to heat the space within the jacket chamber 16. The valve 19 is operated to control the air flow through the jacket chamber 16 and thus the temperature of air within the heat jacket chamber 16 which surrounds the soil samples 36. Throughout the heating process, insulation around the outer surface of the shroud 30 insulates the apparatus 10 from the outside atmosphere, Hot air directed into the heat jacket chamber 16 also ensures even drying and heating of the soil samples 36.

The hot air flowing through the chamber 12 will initially remove moisture from the soil samples 36 to dry the soil sample(s) 35 and as the temperature rises, organic material including organic carbon in the soil samples 36 will be burnt off.

The temperature of air exiting the chamber 12 at the end 14 may be monitored by a temperature sensor 40. When the sensed temperature increases above 100° C. which is the boiling point of water or moisture within the soil samples 36, the soil samples 36 will be dry whilst further heating up to about 550° C. which temperature can be maintained for a period of time will burn off carbon and other organic materials. Removal of all carbon and organic materials from the soil samples can be determined by monitoring the weight of the soil samples 36 by using the weighing device 38 to establish when the weight reaches a point where it does not change.

The weight of the apparatus 10 and soil samples 36 as referred to above can be determined in situ. Thus when the suction pressure applied by the pump 34 is removed from the suction plate 33, the plate 33 will detach from the end 15 of the chamber 13 and allow the apparatus 10 to detach under the influence of gravity from the fixedly mounted heating tube or shroud 30. The suspension elements 39 will thus support only the apparatus 10 plus soil samples 36 and allow the weighing device 38 to determine the total weight of the apparatus 10 and dried soil samples 36 held therein. The change of weight from the initial weight can then be used to enable calculation of the change in weight of the dried and heated soil samples 36 and thus the carbon content originally in the samples 36 or change or carbon content therein. The apparatus 10 and soil samples 36 can be weighed after a given period of time for example 10 minutes and the heating process then repeated until the weight does not vary. Stabilisation of the weight indicates that all carbon and other organic material have been burnt off. The measured weight change correlates to the organic carbon content of the soil samples.

If desired a controller (not shown) may be associated with the temperature sensor 40, suction pump 34 and heating element 31 which will turn the pump 34 off and remove power from the heating element 31 when the temperature sensed at the sensor 40 increases to a selected operating temperature above 100° C. Alternatively when hot air is supplied from an external source, the hot air supply may be turned off automatically depending upon the temperature sensed by the sensor 40.

Figure 7:
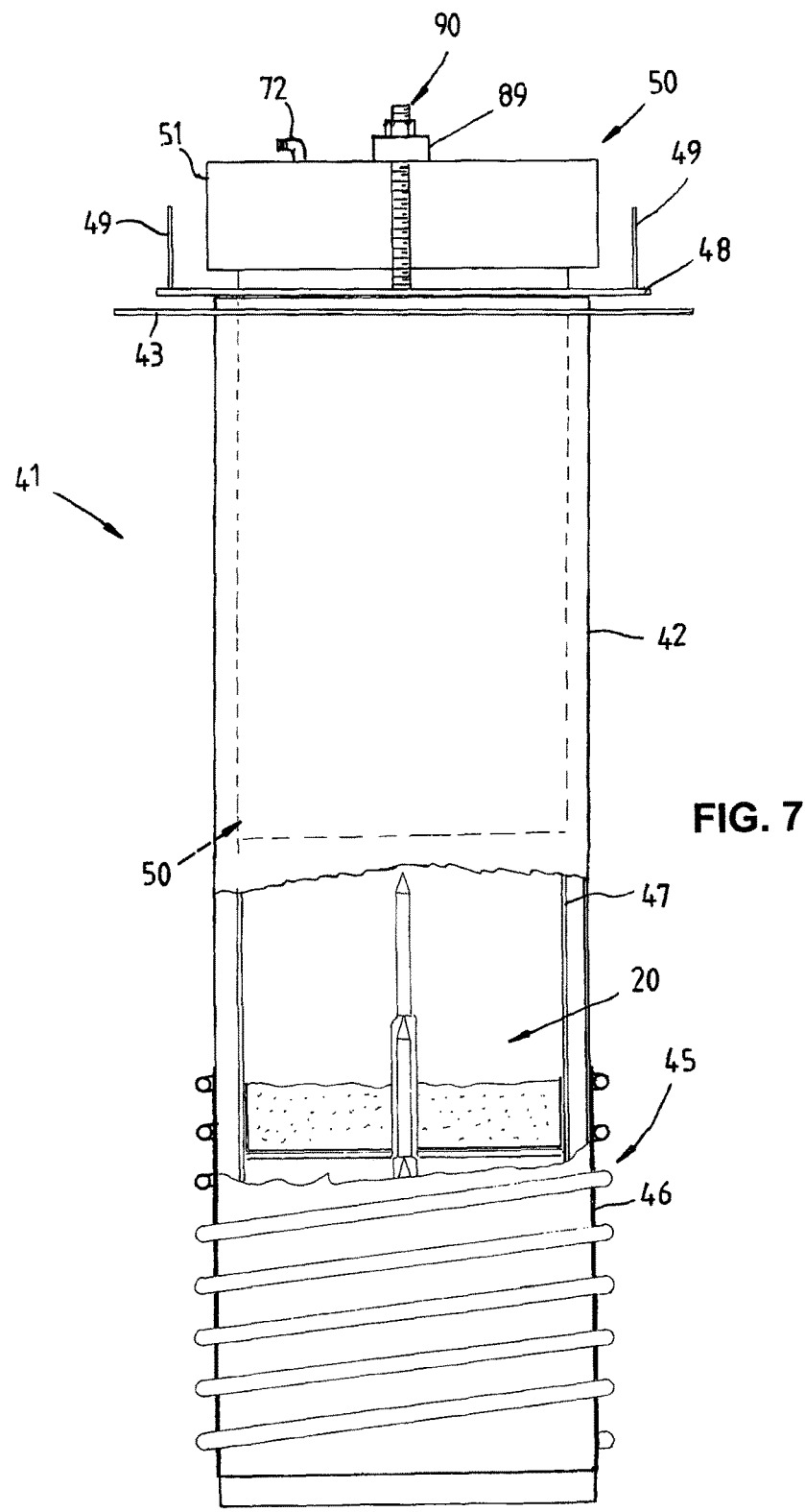
FIG. 7 is a partly cut away view of an alternative apparatus for heating soil samples according to another embodiment of the invention.
Figure 8:
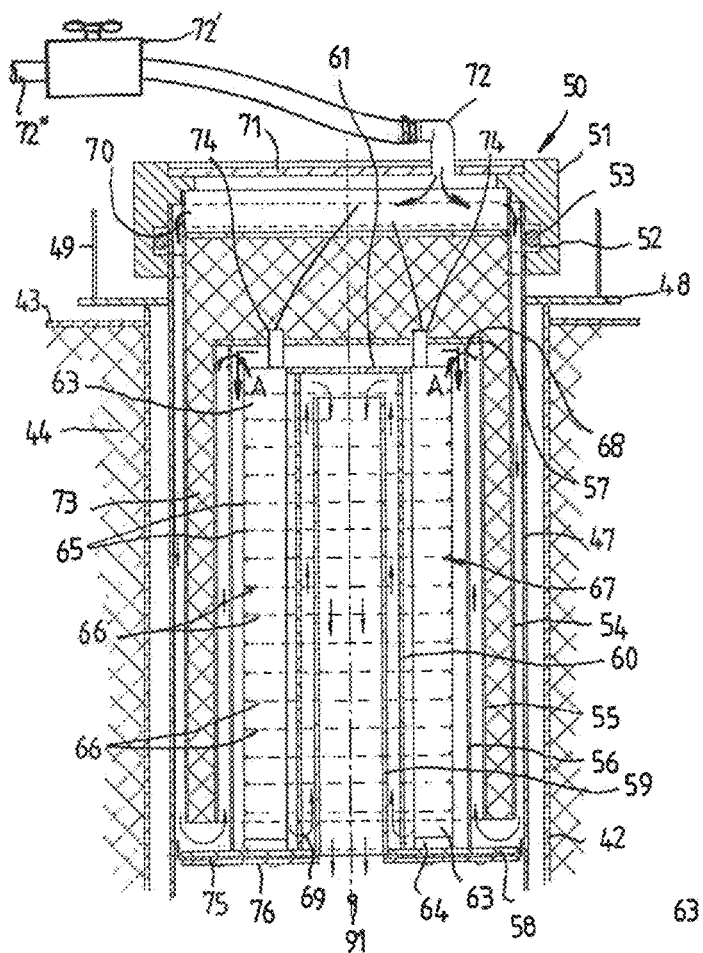
FIG. 8 is a cross-sectional view of the upper end of the soil heating apparatus of FIG. 7 showing the air heating unit.
Figure 10:
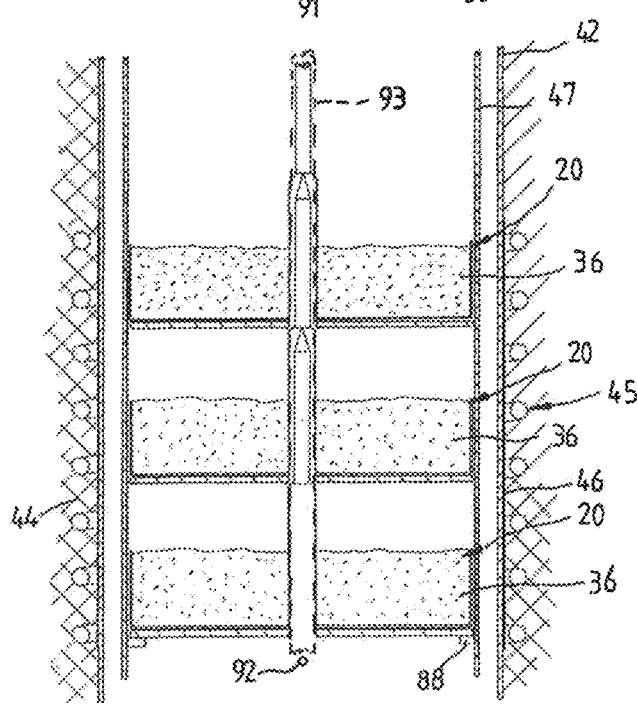
FIG. 10 is a schematic partial cross-sectional view of the lower end of the soil heating apparatus of FIG. 7 showing the series of soil sample holders used in the apparatus.

Referring now to FIG. 7, there is illustrated alternative apparatus 41 for use in heating a sample or samples of soil for the purpose of determining carbon content thereof. The apparatus 41 comprises a main outer elongated tubular housing 42 which is of a circular cross section and which has an annular flange 43 adjacent its upper end. The housing 42 extends a small distance above the flange 43 and is open at opposite ends as also shown in FIGS. 8 and 10. The housing 42 is supported in an upright attitude in any suitable manner for example by being mounted in an external casing and is surrounded by an insulating material 44 (see FIGS. 8 and 10). The insulating material 44 may be rock wool or any other suitable material of combination of insulating materials.

Provided at the lower end of the housing 42 is a secondary heating element 45 which is wound around the housing 42. Interposed between the heating element 45 and housing 42 is a sleeve 46 of heat conducting material which is in firm contact with the outer surface of the housing 42. The heat conducting material which for example may be copper or any other highly heat conducting material serves to distribute heat from the heating element 45 evenly along the lower portion of the housing 42.

The apparatus 41 additionally includes a further elongated housing 47 (equivalent to the housing 11 of FIG. 4) which is received substantially coaxially within the main housing 42. The housing 47 also has an annular flange 48 adjacent its upper end which can seat on the projecting upper end of the housing 42. The annular flange 48 carries spaced apart hangers 49 for suspending the housing 47 in the manner described further below.

A primary heating unit 50 can be inserted into the upper end of the housing 47 and sealed thereto. The primary heating unit 50 includes an annular collar 51 which has an internal annular recess 52 in which an annular seal 53 is located. When the annular collar 51 is in position as shown in FIGS. 7 and 8, the seal 53 seals the collar 51 to the outer surface of the housing 47. The primary heating unit 50 includes a first outer tubular member 54 within the housing 47, a second coaxially arranged tubular member 55 and a third tubular member 56 arranged coaxially within the member 55, the members 55 and 56 being secured to a top disc 57 whilst the lower end of the member 56 is secured a lower annular end member 58. The member 58 supports further inner and outer tubular members 59 and 60 which are arranged coaxially within the member 56.

Figure 9:
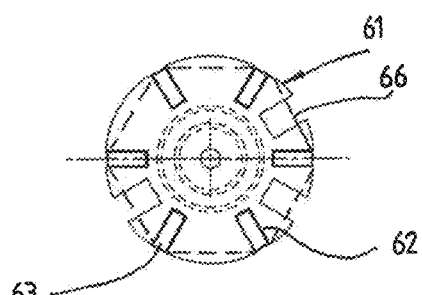
FIG. 9 is a view along line A-A of FIG. 8.

The tubular member 60 carries at its upper end a further disc shaped member 61 which has a series of circumferentially spaced slots 62 in its periphery (see FIG. 9). A series of coil formers 63 are located at their upper ends in the slots 62 and are located at their lower ends by spaced stops 64 on the member 58. The formers 63 are provided in their outer periphery with a plurality of spaced apart slots 65 and a heating wire or element 66 is wound circumferentially around the formers 63 to form an air heater 67 in the space between the tubes 56 and 60. Openings 68 and 69 for the passage of air are provided at the upper end of the tube 56 and lower end of the tube 60. Further openings 70 are provided at the upper end of the tube 54 to communicate with the interior of the collar 51. The collar 51 is provided with a cap 71 which carries a connector 72 for connection via a variable control valve 72' to a compressed gas or air source 72" such as a compressor. An insulting material 73 such as rock wool is also provided between the tubes 54 and 55 and between the upper end of the disc 68 and collar 51. The disc 68 also carries terminals 74 for connecting the heater wire or element 66 to a source of power.

A sealing material or fabric 75 is sandwiched between the member 58 and a further annular member 76, the material or fabric 75 extends radially outwardly to seal against the inner wall of the housing 47 so that the lower end of the heater unit 50 can be sealed to the inner surface of the housing 47.

In use when compressed gas such as compressed air is supplied from the compressed air or gas source to the inlet connector 72 via the valve 72 and current is supplied to the heater 67, air passes as indicated by the arrows through the openings 70 down between the tubes 47 and 54, up between the tubes 55 and 56, through the openings 68 and down through the air heater 67, through the openings 69 and upwardly between the tubes 59 and 60 where it is again heated and down through the tube 59 to exit at the lower end of the heating unit 50.

Referring now to FIG. 10, there is illustrated a series of soil sample holder assemblies 20 which are arranged in use within the housing 47 towards the lower end of the housing 47. The soil sample holder assemblies 20 are of the same configuration as the holder assemblies 20 described with reference to FIGS. 2 to 4 and accordingly like components have been given like numerals. The sleeve 46 extends along the lower end of the housing 42 for a sufficient length such that heat from the secondary heating element 45 can be distributed evenly to the soil samples 36 carried by the holder assemblies 20.

Figure 11:
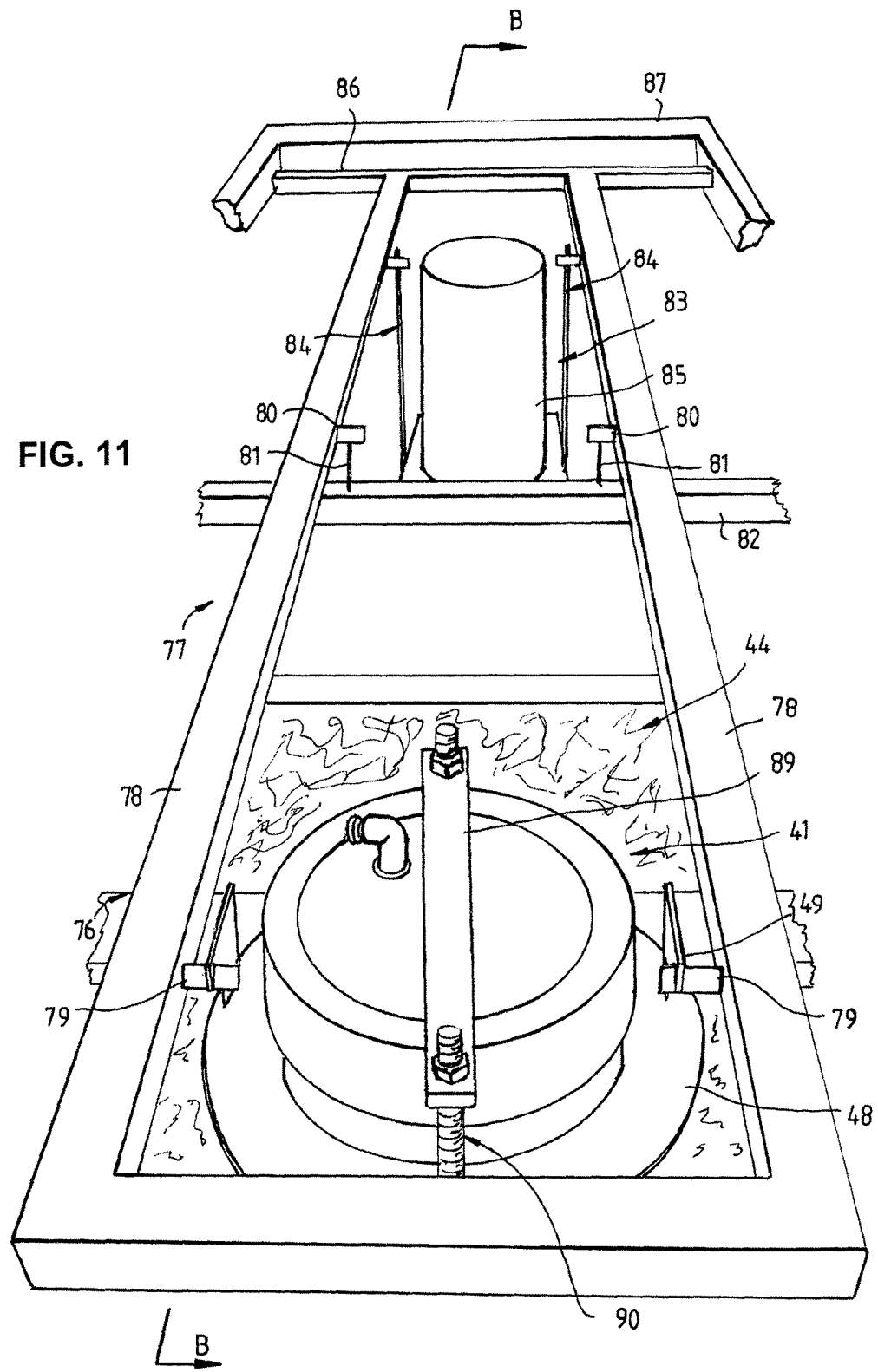
FIG. 11 is a perspective view showing the weighing apparatus for weighing or determining the change of weight of soil samples in situ.

The soil holding and heating housing 47 is suspended or connected by the hangers 49 to one end of a beam 76 of a balance scale 77 as shown in FIG. 11. For this purpose, the beam 76 has opposite parallel arms 78 which have inwardly directed blades 79 defining knife edges on which the hangers 49 can hang. The arms 78 are supported at a fulcrum intermediate its their ends defined by blades 80 providing for knife edge support of the beam 76 on upwardly directed flanges 81 mounted on a support frame 82.

A variable counter or balance weight 83 is supported to the arms 76 on the opposite side of the fulcrum to the apparatus 41 by means of a hanger/knife edge connection 84 similar to that for the housing 47. The apparatus 41 and balance weight 83 are arranged at equispaced positions on opposite sides of the fulcrum of the beam 76. The counter weight 83 may include a beaker or container 85 to which a liquid such as water can be added or removed to balance the beam 76. The end of the beam 76 includes a transverse arm 86 which in the balance position is aligned with an end frame member 87 of the frame 82. The counter or balance weight 83 can also include fixed or variable weights 83' (see FIG. 12).

In use samples of soil 36 taken from an area where carbon content is to be determined is screened to remove all fibrous material such as plant and animal material not yet decomposed and the soil samples are then placed within the holder assemblies 20. The heating unit 50 is removed from the end of the housing 47 and the soil sample holder assemblies 20 and then inserted endwise into the upper end of the housing 47 and slid therealong until the lowermost holder assembly 20 abuts a stop 88 provided at the lower end of the housing 47. The manner of preparation of the soil samples, their location within the holder assembly 20 and the placement of the holder assemblies 20 within the housing 47 is similar to that described with reference to FIGS. 2 to 4.

The heating unit 50 is then placed into the housing 47 from the top so that it seals through the seal 53 to the upper end of the housing 47. The unit 50 will also seal through the sealing member 75 at its lower end to the housing 47. Usually at this time the sample containing housing 47 has been previously located substantially coaxially within the housing 42 and hung via the hangers 49 from the beam 76. The collar 51 of the heating unit 50 may be clamped to the housing 47 by means of a clamping bar 89 and studs/nuts 90 which extend upwardly from the flange 48.

For heating of the soil samples, the collar 51 and housing 47 suspended on the beam 76 are initially urged downwardly into the outer housing 42 until the flange 48 seats on the upper end of the housing 42 as shown in FIGS. 7 and 8. In this position as shown in FIG. 12, the beam 76 will not be in balance and a weight may be applied to the apparatus 41 to maintain the unit in the position of FIGS. 7, 8 and 12. In this position, the annular space between the housings 42 and 47 will be closed or sealed at its upper end to prevent upward flow of air in this space. Current can then be applied to the heating unit 50 and compressed air or gas supplied from the compressed air or gas source 72" via the control valve 72' to the connector 72 for supplying air to the heating unit 50. Air will be forced past the element or wire 66 to be heated and exit at the lower end of the heating unit 50 and the heated air will then be forced through the soil samples 36. Initially the heating unit 50 is operated to remove moisture from the soil samples 36 to dry the soil sample(s) 36. When the sensed temperature increases above 100° C. which is the boiling point of water or moisture within the soil samples 36, the soil samples 36 will be dry. The weight holding the apparatus in the position of FIGS. 7, 8 and 12 is removed and weight may be applied to the counter weight 83 for example by adding liquid to the beaker 85 until the beam 76 is balanced for example as shown in FIG. 13, This provides an indication of the weight of the soil samples 36 after the drying process and prior to the carbon removal process.

After the initial drying and weighing process, the apparatus 41 is moved back to the position of FIG. 13 and increased current is supplied to the heating unit 50 along with increased flow of air or gas from the source 72 to increase the temperature of air exiting the heating unit 50. In addition, current can be supplied to the lower heating element 45 to heat the soil samples 36 at the lower end of the housing 47. As the temperature rises, carbon and other organic materials in the soil samples 36 will be commenced to be burnt off.

The temperature of air exiting the heating unit 50 and at the lower end of the housing 47 after it passes through the soil samples 36 is monitored by temperature sensors 91 and 92 (FIGS. 8 and 10). Typically the samples 36 are heated to temperatures above or in the region of 525° C. and maintained at those temperatures for an extended period of time for example 10-60 minutes to ensure that carbon and other organic materials are burnt off. This temperature and time however can be varied by varying current supply to the heater elements 67 and 45 or by only using one heater element, and also by varying the air or gas supply via the valve 72'. To ensure that the temperature of the soil samples does not increase beyond predetermined limits, the valve 72' is operated to restrict gas flow through the samples. This restricts the volume of oxygen supply to thereby prevent excessive burning of materials within the soil samples. The heating time and temperature of air or gas supplied may also be varied depending up the samples being tested.

As the heating process causes carbon in the soil to be removed by being burnt off, the weight of the heating unit 41 (including the soil samples 36) as suspended from the beam 76 will after the heating process be less than the original weight and the carbon content of the soil can be determined in situ whilst the soil samples 36 and unit 51 are still at a high temperature. Thus the unit 51 may be released from its FIG. 12 position and weight removed from the counter/balance weight 83 for example by removing liquid from the beaker 85 until balance is achieved as shown in FIG. 13. The location of the apparatus 41 within the outer housing 42 will allow the apparatus to move upwardly freely within the housing 42 when weight is removed from the counter/balance weight 83. It will be noted that in the balance position, the arm 86 is in horizontal alignment with the frame member 87. The weight of the liquid removed to achieve balance will correlate to the weight of the organic carbon in the soil.

The location for soil samples to be taken may be determined randomly and preferably at a distance not greater than 10% of the distance from the geometric centre of each nominated area. Subsequent test samples may then be obtained from locations at a random distance, and in a random direction from previous tests.

Remuneration in a program which rewards carbon dioxide sequestration may be calculating by testing soil samples as above to determine the organic carbon content of the soil at the pre-nominated depth then calculating the carbon dioxide equivalent per hectare (or per acre) increase from the previous test.

It will be appreciated that the apparatus of the invention may be in many different configurations other than that illustrated and described to perform the method of the invention, that is heating soil samples by forcing hot air through the samples to dry the samples and/or remove carbon from the samples. Whilst the apparatus 10 has been described for drying/heating three soil samples, it may be used to measure the change of weight of one or more soil samples. Further different air or gas permeable means may be provided for supporting the soil samples 36 within the housing 47.

Figure 4:
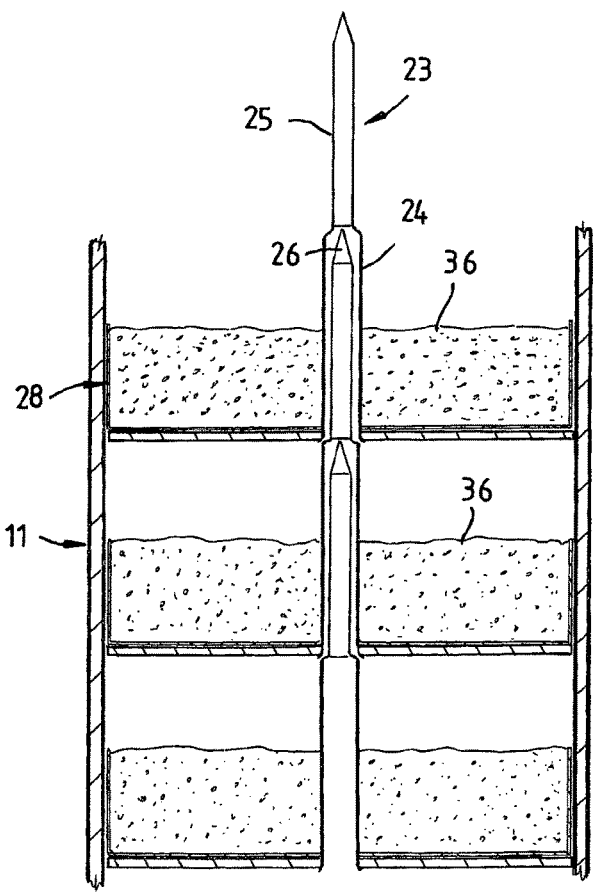
FIG. 4 is a schematic partial cross-sectional view showing a series of soil sample holders engaged with each other within the soil sample heating apparatus.
Figure 14:
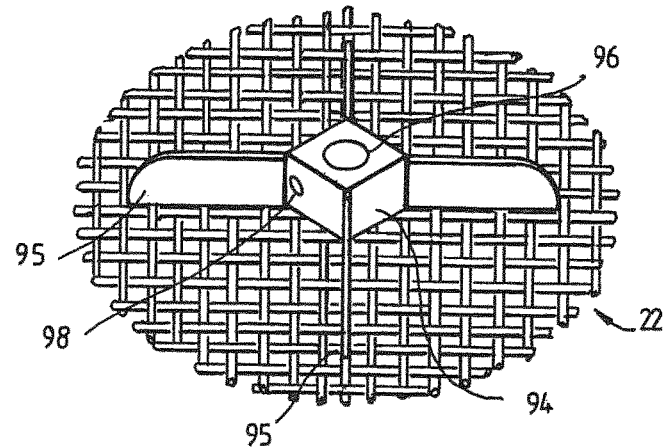
FIG. 14 is an underside view of an alternative soil sample holder.
Figure 15:
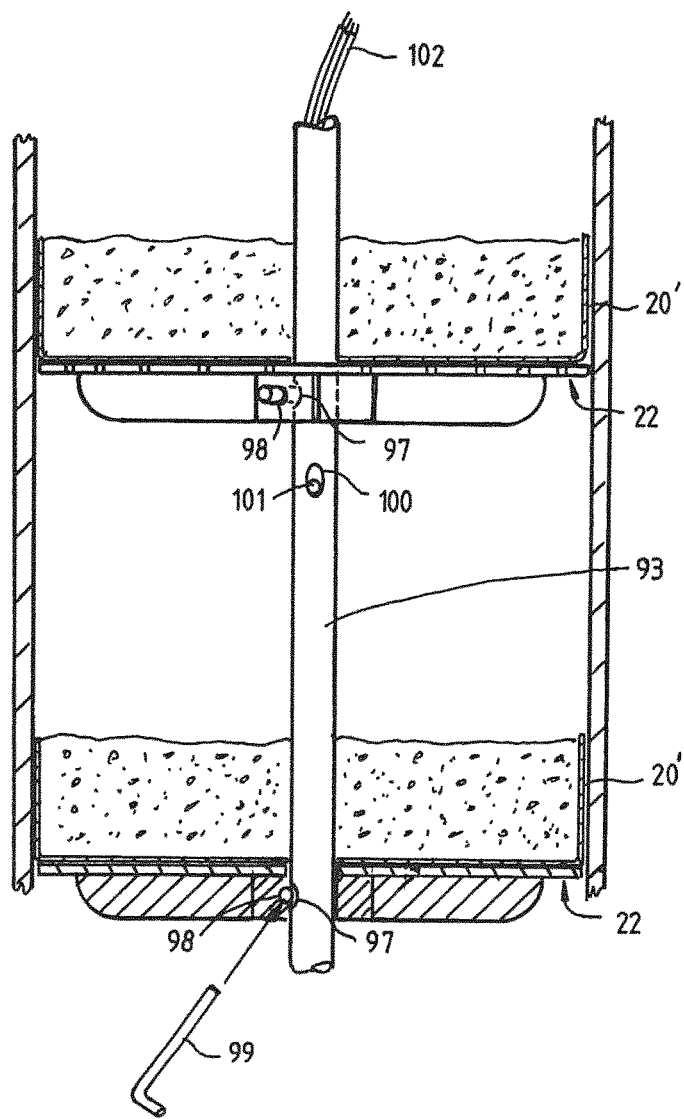
FIG. 15 is a schematic partial cross-sectional view of portion of an alternative soil sample heating apparatus similar to that of FIG. 10.

The soil sample holders 20 may be in different configurations from that shown and described with reference to FIGS. 2, 4 and 10. For example as shown in FIG. 15 (and also in dotted outline in FIG. 10) a support shaft 23 for each grid or mesh member 22 may be replaced by a single central shaft 93 along which respective grid or mesh members 22 may be located at different longitudinal positions. The members 22 may be fixed to the shaft 93 or may be adjustable along the shaft 93 and fixed at various positions along the shaft 93. For this purpose, sleeves may be fixed to the members 22, the sleeves being slidable along the shaft 93 and being fixable in position by grub or clamping screws to the shaft 93. Alternatively and as shown in FIG. 14, a grid or mesh member 22 may have a centrally mounted boss 94 fixed to its underside and from which respective grid supporting ribs 95 extend radially outwardly. The boss 94 has a central aperture 96 to slidably locate the boss 94 and supported grid or mesh member 22 over the shaft 93.

The shaft 93 additionally is provided in its outer surface with spaced rebates or holes 97 and the central boss 94 includes an opening 98 which extends generally tangentially to the aperture 96. A stop pin 99 can be inserted into the opening 98 to locate within a rebate or hole 97 to lock the boss 94 and grid or mesh member 22 in a fixed position to the shaft 93.

The shaft 93 may also be hollow and be provided with spaced elongated apertures or slots for receipt of temperature sensors 101. Temperature sensors 101 may be located above the soil sample holders 20' and below each soil sample holder 20' for temperature monitoring purposes. Wires or cables 102 may be passed through the interior of the shaft 93 for connection to the temperatures sensors 101 for temperature monitoring purposes.

Many different arrangements may also be used for the weighing of the soil sample or samples or apparatus or housing which contains the soil sample or samples other than the arrangement described. Further the described weighing arrangements may be varied from that shown. For example the balance beam 76 may be provided with a pointer and scale to determine change in weight. Alternatively electronic weight sensing means may be employed.

The components of the apparatus may be formed of any suitable material which can resist heat encountered in the apparatus. Typically the components are formed of mild steel or stainless steel.

Typically the compressed gas source comprised compressor which supplies compressed air however the compressed gas source may be a source of any inert gas such as oxygen or a mixture of oxygen and nitrogen. A gas containing oxygen however will be necessary to enable organic materials to burnt off in the testing process.

Any reference to prior art herein is not to be taken as an acknowledgement that such art constitutes common general knowledge.

The terms "comprising" or "comprises" as used throughout the specification and claims are taken to specify the presence of the stated features, integers and components referred to but not preclude the presence or addition of one or more other feature(s), integer(s), component(s) or group thereof.

Whilst the above has been given by way of illustrative embodiment of the invention, all such variations and modifications thereto as would be apparent to persons skilled in the art are deemed to fall within the broad scope and ambit of the invention as herein defined in the appended claims.

The invention claimed is:

1. Apparatus for determining the organic carbon content of soil using loss-on-ignition, said apparatus comprising a housing defining an elongated upright tubular chamber, said chamber having an upper end and a lower end, one or more gas permeable barriers for supporting one or more samples of said soil respectively within said chamber, the or each said gas permeable barrier extending across and between opposite sides of said chamber, means for at least one of generating or supplying a heated gas, and a pump for causing said heated gas to flow through said chamber from said upper end to said lower end thereof and through the soil sample or samples supported on said gas permeable barrier or barriers so as to permit said soil sample or samples to be initially heated to a first lower temperature to remove moisture and dry said one or more soil samples and subsequently heated to a higher temperature whereby organic materials including organic carbon can be removed by being burnt off from the one or more soil samples and means for measuring the change of weight of said housing including said one or more soil samples to provide from the change of weight of said one or more soil samples an indication of organic carbon content in the soil.

2. Apparatus as claimed in claim 1 wherein the or each said gas permeable barrier comprises a soil sample holder which includes at least one of a grid or grating.

3. Apparatus as claimed in claim 2 and including a plurality of gas permeable barriers each comprising a soil sample holder, said holders being arranged at spaced apart longitudinal positions along said chamber.

4. Apparatus according to claim 3 wherein each said soil sample holder includes a central shaft, said central shafts of adjacent said soil sample holders being interengaged with each other so that said soil sample holders are spaced longitudinally within said chamber.

5. Apparatus as claimed in claim 3 wherein said soil sample holders are supported on a common shaft, said common shaft being provided with a plurality of spaced apart holes and wherein each said soil sample holder includes one of a boss or sleeve adapted for slidable location over said shaft, and stop means on at least one of said soil sample holders for cooperation with at least one of said holes to locate said at least one soil sample holder along said shaft.

6. Apparatus as claimed in claim 3 wherein said shaft is hollow and carries one or more temperature sensors adapted to be located respectively in one or more slots provided in said shaft.

7. Apparatus as claimed in claim 2 wherein the or each said gas permeable barrier comprises at least one of a pliable gas permeable material or pad for supporting a said soil sample on said at least one of a grid or grating, said at least one of said material or pad being adapted to form a seal with said chamber to ensure said heated gas passes through a soil sample held by said at least one of said material or pad.

8. Apparatus as claimed in claim 1 wherein said means for at least one of generating or supplying said heated gas includes a gas heating device at one end of the chamber and wherein said pump comprises a suction pump at the opposite end of the chamber for drawing gas through the gas heating device and for causing said heated gas to pass through said soil samples in said chamber.

9. Apparatus as claimed in claim 1 wherein said means for measuring comprises means for weighing the housing containing said soil sample(s) before and after the carbon removal process to enable calculation of the change of weight in the soil sample(s) in situ to provide an indication of carbon content in the soil sample(s).

10. Apparatus as claimed in claim 1 wherein said means for measuring the change in weight comprising a beam balance having a beam which has a central fulcrum, means on one side of said fulcrum for supporting said housing and means on the opposite side of said fulcrum for carrying a counter or balance weight.

11. Apparatus as claimed in claim 10 wherein said housing is suspended from said beam on said one side of said fulcrum and is located substantially coaxially within an upright outer tubular member, said housing being is capable of being moved longitudinally of the outer tubular member in a first direction during balancing of said beam.

12. Apparatus as claimed in claim 11 wherein said housing includes an annular flange adapted to seat on the upper end of said outer tubular member to limit movement of said housing in a direction opposite said first direction.

13. A method of obtaining an indication of the organic carbon content of soil to enable changes in organic carbon content to be determined, said method including the steps of placing a sample or samples of said soil on one or more said gas permeable barrier of the apparatus as claimed in claim 1, operating said pump to cause said heated gas initially at a temperature of up to 110° C. to flow through said chamber and thus through said soil sample or samples to initially dry said soil sample or samples and thereafter at a temperature of up to 550° C. to remove organic materials including organic carbon from said soil sample or sample, and obtaining from the change of weight of the soil sample or samples, an indication of the organic carbon content in the soil.

14. A method as claimed in claim 13 wherein the flow of gas through the sample or samples is controlled to prevent the temperature of the soil samples increasing beyond predetermined maximum limits to avoid excessive burning of materials in the soil sample or samples.

15. A method of obtaining from change in weight of a soil sample or samples an indication of the organic carbon content thereof using loss-on-ignition, said method comprising the steps of locating said soil sample or samples on one or more gas permeable barriers respectively provided within an upright chamber of an elongated housing, forcing heated gas through said chamber from an upper end to a lower end thereof and through said soil sample or samples to initially dry said sample or samples and subsequently to remove organic carbon from said soil sample or samples and measuring the change in total weight of said housing and said soil sample or samples after drying and after the carbon removal process due to said heating of said soil sample or samples without removing said sample or samples from said housing to provide an indication of organic carbon content of the initial soil sample or samples.

16. A method as claimed in claim 15 where for drying of said soil sample or samples, said heated gas is passed through the soil sample or sample for a sufficient time and at temperatures up to approximately 100° C. to 110° C. until the weight of the housing containing said soil sample or samples ceases to change.

17. A method as claimed in claim 16 where for removing organic materials including organic carbon from said soil sample or samples, said heated gas is passed through the soil sample or sample for a sufficient time and at the temperatures up to approximately 550° C. until the weight of the housing including said soil sample or samples ceases to change.

* * * * *